United States Patent [19]

Tsai et al.

[11] Patent Number: 4,831,128

[45] Date of Patent: May 16, 1989

[54] SYNTHETIC HOMO- AND HETEROPOLYSACCHARIDES AND A METHOD FOR THE PREPARATION THEREOF

[75] Inventors: John J. Tsai, Belle Mead; Martin M. Tessler, Edison, both of N.J.

[73] Assignee: National Starch and Chemical Corporation, Bridgewater, N.J.

[21] Appl. No.: 882,130

[22] Filed: Jul. 3, 1986

[51] Int. Cl.$^4$ ............................................. C08B 31/08
[52] U.S. Cl. .................................. 536/111; 536/102; 536/114; 536/124
[58] Field of Search ........................... 536/119, 111

[56] References Cited

U.S. PATENT DOCUMENTS

| | | |
|---|---|---|
| 2,976,274 | 3/1961 | McNeely et al. .................. 536/114 |
| 3,467,647 | 9/1969 | Benniga et al. ................... 536/114 |
| 3,723,408 | 3/1973 | Nordgren et al. ................. 536/114 |
| 3,823,100 | 7/1974 | Rothwell et al. ................. 536/114 |
| 3,912,715 | 10/1975 | Jarowenko ....................... 536/114 |
| 3,931,148 | 1/1976 | Langdon ......................... 260/210 |
| 4,031,307 | 6/1977 | DeMartino et al. .............. 536/114 |
| 4,237,271 | 12/1980 | Rayford et al. ................... 536/111 |
| 4,663,448 | 5/1987 | Chiu ............................... 536/111 |
| 4,673,707 | 7/1987 | Tsai et al. ........................ 525/54.2 |

FOREIGN PATENT DOCUMENTS 625644 7/1949 United Kingdom .

OTHER PUBLICATIONS

Bollenback, G. N., "Glycosidation", Methods in Carbohydrate Chemistry, vol. II, Academic Press, N.Y., 1963, pp. 326, 327.
Sandford et al., "Fungal Polysaccharides", pp. 250-268, (1980).
Erne, K., "Studies on Glycosides and Isopropylidene Derivatives"; Acta Chemica Scandinavica, 9, (1955), pp. 893-901.
Bochkov, A. F., "Chemistry of the O-Glycosidic Bond", Pergamon Press, (1979), pp. 14-15.
Cadotte, J. E. et al., (JACS, 74), pp. 1501-1504, (1952).
"The Carbohydrates", editors W. Pigman and D. Horton, vol. IIA, 2nd Ed., Academic Press, New York, (1970).

Primary Examiner—Johnnie R. Brown
Assistant Examiner—Elli Peselev
Attorney, Agent, or Firm—Edwin M. Szala; Lori D. Tolly

[57] ABSTRACT

Mono- and polysaccharides comprising one to about 20 saccharide units which also contain a reducing carbon atom are reacted with 3-halo-1,2-propandiol in the presence of a cation exchange resin to form 3-halo-2-hydroxypropyl glycosides or glycidyl glycosides. These glycosides react with natural polysaccharides such as starch and plant gums to form novel synthetic homo- and heteropolysaccharides with pendant saccharide side chains.

18 Claims, No Drawings

SYNTHETIC HOMO- AND HETEROPOLYSACCHARIDES AND A METHOD FOR THE PREPARATION THEREOF

This application is a continuation-in-part of application Ser. No. 577,463 filed Feb. 6, 1984 now abandoned.

BACKGROUND OF THE INVENTION

This invention relates to novel synthetic homo- and heteropolysaccharides and to a method for their preparation.

There are many heteropolysaccharides which occur naturally. Heteropolysaccharides including such substances as carrageenan, xanthan, gum arabic and guar gum which are obtained from various botanical, algal, and microbial sources each exhibit unique rheological thickening and solution stabilizing properties influenced by their polymer configuration. While new microbial heteropolysaccharides having potential utility in industry are continuously being discovered, few are actually employed in commerce due to the difficulty involved in producing them on a large scale economically.

Various synthetic polysaccharides possessing saccharide or oligosaccharide unit side chains have been prepared. For instance, H. Roberts, "Starch: Chemistry and Technology", Vol. II, Academic Press, New York (1967), pg. 332 teaches that amylose has been substituted with side chains of amylose, d-glucose, maltose, or cellobiose as well as longer chains containing 3 or more d-glucose units by such methods as alkali-catalyzed transglycosidation from phenyl pyranosides, or silver perchlorate catalyzed displacement of trityl groups on anylose by poly-O-acylglycosyl bromides. Acid catalyzed transglycosidation to introduce d-galactose units into an amylopectin molecule is also described.

An art-recognized method of glycoside preparation is to selectively protect all the hydroxyl groups of the saccharide (i.e. by acetylation) except for the hydroxyl of the reducing end group which may be halogenated or orthoesterified, prepare the glycoside and then remove the protecting groups. While this method is used in the preparation of mono- and disaccharide glycosides, selective protection of hydroxyl groups of larger polysaccharides is an impractical, if not impossible, first step in glycoside synthesis.

Glycosides have also been prepared without protecting all the saccharide hydroxyl groups by reacting mono- or polysaccharides with an alcohol in the presence of a strong acid catalyst at elevated temperatures. See U.S. Pat. No. 3,931,148 issued Jan. 6, 1976 to W. Langdon which describes the preparation of 3-chloro-2-hydroxypropyl mono- and polysaccharide glycosides by reacting monosaccharides and polysaccharides which are hydrolyzable to monosaccharides with 3-chloro-1,2-propandiol (also commonly referred to as 3-chloro-1,2-propanediol) and from about 0.01 to 2.0 weight percent, based on the reactants, of an acid catalyst. Useful catalysts suggested included the following low molecular weight acids: hydrochloric acid, sulfuric acid, methane sulfonic acid, phosphoric acid, toluene sulfonic acid, and boron trifluoride. The procedure, which will be described in more detail in the following examples produces severely hydrolyzed products which are a dark color, probably due to charring caused by the acid at high reaction temperatures. The degradative effect of the procedure on saccharides is acknowledged in the reference as polysaccharides of starch and cellulose (which contain anywhere from 200 to over 6,000 saccharide units) are suggested as useful starting materials for glycosides which ultimately contain, at maximum, only 20 saccharide units. See also U.K. Pat. No. 625,644 to A. Chwala which describes the preparation of various glucosides by reacting a $C_2$-$C_5$ alcohol containing at least one halogen atom with a mono- or polysaccharide in the presence of a low molecular weight acid catalyst having a dissociation constant below that of hydrochloric acid.

Cation exchange resins have been employed as catalysts in the preparation of monosaccharide glycosides. For example, G. Bollenback, "Glycosidation", Methods in Carbohydrate Chemistry, Academic Press, Inc., New York, Vol. II, 1963, pages 326-327, describes the preparation of methyl-D-glucopyranoside by reacting anhydrous D-glucose with methanol at reflux in the presence of a cation exchange resin and recovering the glycoside. Bollenback reports that resins such as sulfonated crosslinked polystyrenes, sulfonated phenolics and sulfonated coals can be successfully used as catalysts in this condensation reaction. They may then be removed by filtration and later reused.

The use of cation exchange resins in the preparation of mono- and disaccharide glycosides is also described in Acta Chemica Scandinavica, 9 (1955), pages 893–897. When glucose was reacted with methanol in the presence of a sulfonated polystyrene type resin, an α-methyl-D-glucopyranoside was obtained in high yields. Maltose and lactose were similarly reacted. The disaccharides were degraded resulting in the methyl glycosides of their monosaccharide components. When the preparation of the methyl glycoside of fructose was attempted, the monosaccharide was rapidly degraded.

It is an object of the present invention to provide an improved method for preparing 3-halo-2-hydroxypropyl glycosides of monosaccharides and short chain polysaccharides.

It is a further objective to prepare novel synthetic homo- and heteropolysaccharide ethers having pendant saccharide side chains.

SUMMARY

We have now found that cation exchange resins are useful as catalysts in the synthesis of polysaccharide glycosides. By employing a cation exchange resin, polysaccharide glycosides may be prepared without the problems experienced in the prior art.

The above objects are achieved by reacting monosaccharides or polysaccharides comprising no more than about 20 saccharide units which contain one reducing carbon atom with an excess of 3-chloro-1,2-propandiol or 3-bromo-1,2-propandiol in the presence of a cation exchange resin to produce 3-halo-2-hydroxypropyl glycosides wherein the 3-halo-1,2-propandiol is joined to the saccharide unit through an acetal or ketal linkage at the reducing carbon atom. These halohydrin propyl glycosides or the corresponding glycidyl glycosides obtained upon ring closure may then be reacted with polysaccharides to form novel synthetic homo- and heteropolysaccharides with pendant saccharide side chains attached by ether linkages represented by the formula:

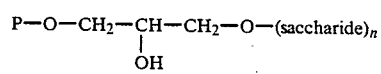

where P-O represents a polysaccharide molecule selected from the group consisting of starch and plant gums with the oxygen being linked to the polysaccharide molecule by an ether linkage, (saccharide)$_n$ represents a saccharide unit with n being from 1 to about 20, and with the oxygen being linked to the reducing glycosidic carbon atom of (saccharide)$_n$ by an acetal or ketal linkage.

The monosaccharides which may be employed in the preparation of the glycoside reagent include glucose, fructose, sorbose, mannose, galactose, talose, allose, altrose, gulose, idose, arabinose, xylose, lyxose, ribose, and other similar monosaccharides. Polysaccharides which may be employed in the preparation of the glycosides include maltose, gentiobiose, lactose, cellobiose, maltodextrins of starch having a dextrose equivalent (D.E.) of 5 or greater and other similar polysaccharides comprising no more than about 20 saccharide units.

In one method, novel starch derivatives are prepared by reacting an aqueous slurry of a starch base with about 0.1 to 100% by weight, based on dry starch, of 3-halo-2-hydroxypropyl glycoside and/or glycidyl glycoside under alkaline conditions and isolating the resulting starch derivative. Under these conditions the glycoside reacts with the free hyroxyl groups of the starch polymer to produce starch ether derivatives with pendant saccharide side chains. The reaction is carried out at a pH of 11–13 preferably at a temperature of 25°–45° C. for 6 to 16 hours.

In another method, novel gum derivatives are similarly prepared by reacting for example, a polygalactomannan guar gum with about 0.1 to 100% by weight, based on dry gum, of the glycoside and isolating the resulting gum derivative. The reactions are carried out under alkaline conditions in an aqueous solution containing a water-miscible solvent.

DETAILED DESCRIPTION OF THE PREFERRED EMBODIMENTS

Glycosides may be prepared from mono- and polysaccharides which contain a reducing carbon atom. This carbon atom, which is located in the terminal saccharide ring, is capable of reacting with alcohol to form glycosidic products attached by an acetal or ketal linkage, depending on the mono- or polysaccharide employed.

The glycosides herein are prepared by reacting 3-halo-1,2-propandiol with mono- or polysaccharides in the presence of a cation exchange resin. By employing a cation exchange resin, mono- and polysaccharide glycosides may be prepared at moderate temperatures without charring as evidenced by the light colored products obtained. Additionally no neutralization step is required as in acid catalyzed systems as the catalyst may be easily recovered by filtration. Moreover, glycosides of polysaccharides may be produced with only minimal degradation occurring.

A. Glycoside Preparation

The process comprises reacting a mono- or polysaccharide in an excess of 3-halo-1,2-propandiol in the presence of a cation exchange resin. The reaction is conducted with stirring at a temperature of about 55°–80° C., preferably 60°–65° C. over a period of about 3–20 hours, preferably 6–8 hours. It was discovered by employing the preferred lower temperatures and shortened reaction times, the amount of oligosaccharide formation and polysaccharide degradation is reduced.

After the reaction is complete, the mixture is filtered in order to remove the cation exchange resin. The excess diol may then be removed by a number of methods including, for example, vacuum distillation or washing with organic solvents in order to obtain the 3-halo-2-hydroxypropyl glycoside. When monosaccharide glycoside reagents are prepared, the diol may be removed from the glycoside by vacuum distillation, preferably at a temperature of about 80° C. and a pressure of a 2 mm Hg. After distillation, the glycoside may optionally be washed with an organic solvent such as acetone. Glycosides prepared with polysaccharides may be recovered by vacuum distillation, however distillation temperatures above about 60° C. may cause some degradation. These glycosides are preferably recovered by suspending the glycoside/diol mixture in an organic solvent and filtering a number of times to remove the excess diol and other impurities.

The glycidyl glycosides useful herein may be prepared by reacting a 3-halo-2-hydroxypropyl glycoside with an alkali metal hydroxide in order to form the epoxide group. Typically, the glycoside is mixed with an aqueous alkaline solution while cooling. The mixture is neutralized with acid and later dissolved in alcohol in order to precipitate the metal salts formed. After filtration, the glycidyl glycoside may be recovered by removing the alcohol and water by vacuum distillation.

The halogenated propandiols which may be employed include 3-chloro-1,2-propandiol and 3-bromo-1,2-propandiol. The use of the chloro derivative is prepared due to its commercial availability and cost. The particular saccharide employed and its degree of solubility in the halogenated propandiol will determine the minimum amount of reagent required. While a saccharide to diol ratio of as little as 1:1.4 has been employed, a preferred ratio is at least 1:3 to 1:6, most preferably 1:5. As described above, monosaccharides and polysaccharides of up to about 20 saccharide units which contain a reducing carbon atom are applicable herein. It was found that as the number of saccharide units increases the polysaccharide becomes less reactive and more difficult to dissolve in the 3-halo-1,2-propandiol without employing undesirably high temperatures which causes significant degradation.

Any cation exchange resin may be used in the glycoside preparation. Suitable exchange resins include sulfonated-crosslinked polystyrene such as commercially available Amberlite Ir-120 from Rohm and Haas, Dowex 50 from Dow Chemical and Permutit Q from Permutit; sulfonated phenolics such as Duolite C-3 from Diamond Shamrock; and sulfonated coals such as Zeo Karb H from Permutit. The preferred cation exchange resin is Dowex 50. The amount of resin useful herein is about 1 part resin to 2–8 parts by weight of saccharide, preferably 1 part resin to 4–5 parts saccharide.

The mono- and polysaccharide glycoside reagents herein are capable of reacting with natural polysaccharides including, for example, starches and starch conversion products derived from any plant source; starch ethers and esters; cellulose and cellulose derivatives and various plant gums and gum derivatives.

B. Novel Starch Ether Preparation

The applicable starch bases which may be used in preparing the starch ether derivatives herein may be derived from any plant source including corn, potato, sweep potato, wheat, rice, sago, tapioca, waxy maize, sorghum, high amylose corn, or the like. Also included are the conversion products derived from any of the latter bases including, for example, dextrins, prepared by the hydrolytic action of acid and/or heat; oxidized starches prepared by treatment with oxidants such as sodium hypochlorite; fluidity or thin-boiling starches prepared by enzyme conversion or mild acid hydrolysis; and derivatized starches modified by typical processes known in the art (i.e., etherification, esterification, and crosslinking). The starch base may be a granular starch or a gelatinized starch, i.e. non-granular starch.

The preparation of the monofunctional halohydrin glycoside reagent and its reaction with starch may be represented by Equations I and II, respectively;

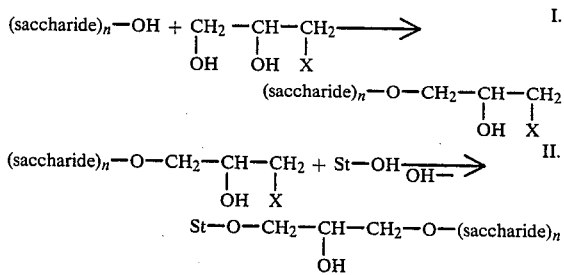

wherein St-O represents a starch molecule, (saccharide)$_n$ represents a saccharide unit where O is attached to the reducing carbon atom of (saccharide)$_n$ with n being 1 to 20 and X is chlorine or bromine.

It should be noted that either the halohydrin glycoside or glycidyl glycoside reagent represented by the following structure:

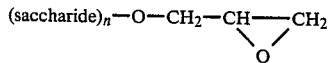

can be used, as the etherification reaction proceeds only under alkaline conditions after the halohydrin group is first converted to the epoxide form. Starch reacted with either a 3-halo-2-hydroxypropyl gluco-glycoside or glycidyl-glucoglycoside, for example, would yield a novel starch ether having randomly occurring pendant saccharide side chains as depicted below:

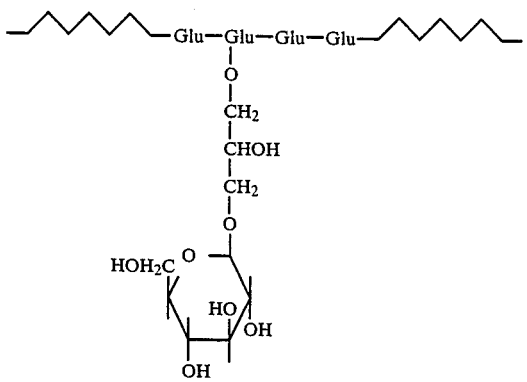

Hence it may be seen that the glucose unit of the glucoglycoside is attached by an acetal linkage at the reducing $C_1$ carbon atom of the glucose molecule.

The partitioner will recognize that the starch molecule is a polysaccharide composed of many anhydroglucose units, each having three free hydroxyl groups (except the non-reducing end glucose units which contain four free hydroxyl groups) which may react with the glycoside reagent. This, the number of such displacements or the degree of substitution (D.S.) will vary with the particular starch, the ratio of reagent to starch, and to some extent, the reaction conditions. Furthermore, since it is known that the relative reactivity of each of the hydroxyl groups within the anhydroglucose unit is not equivalent, it is probable that some will be more reactive with the reagent than others.

The saccharide portion of the glycoside reagent also contains free hydroxyl groups. It should therefore be understood that in the alkali catalyzed polysaccharide etherification reaction, there is a possibility that the glycoside reagent may react with another reagent molecule. Such reaction would yield a saccharide-containing molecule which would still contain an unreacted glycidyl group capable of reacting with starch or other polysaccharide molecule.

The starch reaction may be conducted by a number of techniques known in the art employing, for example, an aqueous reaction medium, an organic solvent medium, or a dry heat reaction technique wherein a wet starch cake is impregnated with the glycoside reagent then subjected to dry heat.

In the preferred method, the reaction is carried out in an aqueous medium using either an aqueous slurry or an aqueous dispersion of the starch base. The glycoside reagent may be added to the reaction mixture as a solid or an aqueous solution. The preferred concentration of the solution is 20–50% by weight, based on the weight of reagent. In an alternative method, the glycoside reagent solution is brought to the desired alkaline pH prior to its addition to the starch base, this being accomplished by the addition of sufficient alkali. In another variation dry starch may be added to an alkaline solution of the glycoside reagent.

The amount of glycoside reagent to be employed in the reaction with the starch herein will vary from about 0.1 to 100% by weight, based on the weight of dry starch, depending on such factors as the starch base used, the glycoside reagent used, the degree of substitution desired in the end product, and, to some extent, the reaction conditions used.

The starch reaction is carried out under alkaline conditions, at a pH of 11–13, preferably 11.4–12.4. Alkali may be added to the starch slurry or dispersion either prior to or after the addition of the glycoside reagent. The pH is conveniently controlled by the addition of sodium hydroxide, potassium hydroxide, calcium hydroxide, ammonium hydroxide, tetramethylammonium hydroxide, and the like. The preferred base is sodium hydroxide.

When conducting the reaction with granular starches, it may sometimes be desirable to carry out the reaction in the presence of salts, e.g. sodium sulfate, in amounts of from about 10 to 40% by weight, based on dry starch. The presence of sodium sulfate acts to suppress swelling of the starch and gives a more filterable product. The sodium sulfate is not used in the calcium hydroxide reactions.

The reaction mixture is agitated under the desired reaction conditions. The reaction time may vary from 0.5 to 20 hours, depending on such factors as the amount of the glycoside reagent employed, the temperature, the pH, the scale of the reaction, and the degree of substitution desired. In general, the preferred range of reaction times is from 6 to 16 hours.

The reaction is carried out at a temperature of from 20°–95° C., preferably 25°–45° C. It will be recognized by the practitioner that the use of temperatures above about 60° C. with granular starches in an aqueous medium will result in granule swelling and filtration difficulties or in gelatinization of the starch. In instances where higher reaction temperatures are desired, an aqueous solution containing a water-miscible solvent may be employed to prevent swelling.

After completion of the reaction, the pH of the reaction mixture is adjusted to a value of from 3 to 7 with any commercial acid such as hydrochloric acid, sulfuric acid, acetic acid, and the like. Such acids may be conveniently added as a dilute aqueous solution.

Recovery of the novel derivatives may be readily accomplished, with the particular method employed being dependent on the form of the starch base. Thus, a granular starch is recovered by filtration, optionally washed with water to remove any residual salts, and dried. The granular starch products may also be drum-dried, spray-dried, or gelatinized and isolated by alcohol precipitation or freeze drying to form non-granular products (i.e. gelatinized). If the starch product is non-granular, it may be purified by dialysis to remove residual salts and isolated by alcohol precipitation, freeze drying, or spray drying.

Observation of the novel derivatives herein in aqueous solution after gelatinization shows that the monofunctional glycoside reagents of the present invention stailize but do not inhibit (i.e., crosslink) the starch products. This highly desired property permits the derivatives of this invention to be utilized for example, in various sizings, coatings, thickening and adhesive applications.

The gelatinization temperature of starch granules in aqueous solution varies with the particular starch type. As the gelatinization temperature of a starch is reached, the granules begin to swell as intermolecular hydrogen bonds weaken and become disrupted. As the starch granules continue to swell, a corresponding increase in clarity, solubility, and viscosity is seen. The introduction of various substituent groups onto the starch molecules of the granule interferes with the associative bonds which hold the granule together. As such, derivatization of starch by monofunctional reagents such as acetic anhydride and propylene oxide of the prior art and the glycosides herein lowers the gelatinization temperature of the starch. The gelatinization temperature of a modified starch in comparison to its underivatized base is a qualitative measure of the degree of derivatization of a starch product. The Brabender Viscoamylograph, an apparatus utilized to measure the viscosity of a starch suspension at various temperatures is also useful for determining gelatinization temperatures. A method for such determination is described hereafter.

C. Novel Gum Ether Preparation

Any natural gum derived from a plant source is applicable herein. Also suitable for use herein are gum degradation products resulting from the hydrolytic action of acid, heat, shear, and/or enzymes; oxidized gums, derivatized gums such as esters or ethers; and other typical carbohydrate modifications. The use of polygalactomannan gums is preferred. These gums are heteropolysaccharides composed principally of long chains of mannose units and single unit side chains of galactose units. The are commonly found in the endosperm of certain seeds of the plant family "Leguminosae", such as the seeds of guar, locust bean, honey locust, flame tree, and the like. They may be used in the form of endosperm "splits", i.e. tough, non-brittle endosperm sections (see U.S. Pat. No. 3,132,681 for a method for separation the splits) or preferably in the form of purified or unpurified ground endosperm (see U.S. Pat. Nos. 2,891,050 and 3,455,899).

The most preferred gums are guar gum and locust bean gum because of their commercial availability. Guar gum is essentially a straight chain mannan wherein the mannose units are linked in a 1,4-$\alpha$-glycosidic linkage and the galactose branching takes place by means of a 1,6 linkage on alternate mannose units (galactose to mannose ratio of 1:2). If desired, guar gum may be purified according to the method described in U.S. Pat. No. 4,031,306, in which case residual nitrogen content will decrease from about 0.7% to less than 0.1%. Locust bean gum has a structure similar to guar gum, wherein the galactose to mannose ratio is 1:4, but wherein the branching is not uniformly spaced.

The practitioner will also recognize that the gum molecule is a polysaccharide containing many anhydro sugar units, each having on the average three available hydroxyl sites which may react with different reactivities with the reagent depending on such factors as the particular gum, amount of reagent employed, and the reaction conditions.

In the method of this invention, the reaction is carried out in a two-phase reaction system comprising an aqueous solution of a water-miscible solvent and water-soluble reagent in contact with the solid polygaloctomannan gum. The water content may vary from 10–60% by weight depending upon the water-miscible solvent selected. If too much water is present in the reaction system, the gum may swell or enter into solution thereby complicating recovery and purification of the gum derivative.

The water-miscible solvent is added in an amount sufficient for the preparation of a gum suspension which can be agitated and pumped. The weight ratio of water-miscible solvent to gum may vary from 1:1 to 10:1, preferably from 1.5:1 to 5:1.

Suitable water-miscible solvents for use herein include alkanols, glycols, cyclic and acylic alkyl ethers, alkanones, dialkylformamide and mixtures thereof. Typical solvents include methanol, ethanol, isopropanol, secondary pentanol, ethylene glycol, acetone, methylethylketone, diethylketone, tetrahydrofuran, dioxane, and dimethylformamide.

The amount of glycoside reagent to be employed in the reaction with the gum herein will vary from about 0.1 to 100% by weight, based on the weight of a dry gum, depending on such factors as the gum used, the reagent used, the degree of substitution desired in the end product, and, to some extent, the reaction conditions used.

The glycoside reagent may be added to the reaction mixture as a solid or an aqueous solution. The preferred concentration of the solution is 20–50% by weight, based on weight of reagent. In an alternative method the glycoside reagent solution is brought to the desired alkaline pH prior to its addition to the gum, this being accomplished by the addition of sufficient alkali. In another variation dry gum may be added to an alkaline solution of the glycoside reagent containing water and a water-miscible solvent.

The gum reaction is carried out under alkaline conditions. Alkali may be added to the gum suspension either prior to or after the addition of the reagent. Typical alkalies include sodium hydroxide, potassium hydroxide, calcium hydroxide, ammonium hydroxide, tetramethylammonium hydroxide, and the like. The preferred alkali is sodium hydroxide. Some of the alkali functions as a reagent, i.e. neutralizes the hydrochloric acid formed when the gum reacts with the reagent, and some of the alkali functions as a catalyst. An excess of alkali is therefore required to catalyze the reaction. The excess alkali which functions as the catalyst can vary in amount from about 0.05 to 20% by weight, based on the weight of fum. This excess alkali is not consumed during the gum etherification reaction.

The reaction is carried out at a temperature of from 15°–100° C., preferably 20°–60° C. The reaction mixture is agitated under the desired reaction conditions. The reaction time may vary from 0.5 to 20 hours, depending on such factors as the amount, stability and reactivity of the glycoside reagent employed, the temperature, the pH, the scale of the reaction, and the degree of substitution desired. In general, the preferred range of reaction time is from 3 to 16 hours.

After completion of the reaction, it is preferred that the excess alkali be neutralized with an acid such a hydrochloric acid, sulfuric acid, acetic acid, citric acid, and the like.

After completition of the etherification reaction, the novel gum ether derivatives are separated from the reaction by centrifugation or filtration. The solid derivative so recovered is preferably further treated and purified by washing with an aqueous solution of water-miscible solvent and then further washing with a more anhydrous form of the same solvent.

The following examples will more fully illustrate the practice of this invention but they are not intended to limit its scope. In the examples, all parts and percentages are given by weight and all temperatures are in degrees Celsius unless otherwise noted. The gelatinization temperature of the starch derivatives was determined by the following procedure:

Gelatinization Temperature Determination

A slurry of 70.4 grams starch (based on anhydrous starch weight) and an amount of distilled water such that a total charge weight of 400.0 grams is obtained is added to a Brabender Visco-Amylograph. The slurry is heated to 30° C. then slowly heated at a rate of 1.5° C. per minute. The gelatinization temperature is recorded as the temperature when the slurry reaches a viscosity of 100 Brabender units.

EXAMPLE 1

This example illustrates the preparation of 3-chloro-2-hydroxy-propyl glucoglycoside.

To a 0.5 liter round-bottom flask equipped with condenser, mechanical stirrer and means for heating, there was added 80 g. (0.44 mole) of dextrose, 237 g (2.15 moles) of 3-chloro-1,2-propandiol, and 20 g Dowex 50W-X8 cation exchange resin (4.83 meq/g) in H+ form. The mixture was heated to 60° C. and stirred at that temperature for 16 hours. The reaction mixture was cooled and then filtered over a gauze cloth to remove the resin. The reaction mixture was clear and light yellow in color. Unreacted diol was removed by vacuum distillation at 80° C. at 2 mm Hg. The hygroscopic solid product was slurried in acetone and filtered three times to remove residual impurities then dried in a vacuum dessicator. The light beige colored glycoside was recovered in an 80% yield (based on theoretical). $^{13}$C-NMR spectral analysis indicated the absence of the reducing carbon atom hemi-acetal signals at 92 and 96 ppm. Signals were recorded indicating a glycosidic carbon at 100.2 and 104.3 ppm corresponding to an acetal linkage. Organic chlorine analysis indicated 11.5% organic chlorine instead of the expected value of 13.02% based on a 272.54 molecular weight of the glycoside. This indicates that a small degree of oligosaccharide formation occurred resulting in a product containing both the glucoglycoside as well as a small amount of oligosaccharide glycoside.

EXAMPLE 2—Comparative

This example illustrates the preparation of 3-chloro-2-hydroxypropyl glucoglycoside by employing a strong acid catalyst instead of a cation exchange resin of the above Example 1.

A procedure similar to those described in U.S. Pat. No. 3,931,148 (mentioned above) was employed. To a 1-liter round bottom flask equipped with condenser, mechanical stirrer and heating means, there was added 90 g (0.5 mole) of dextrose, 55.3 g (0.5 mole) of 3-chloro-1,2-propandiol and 0.5 g of concentrated sulfuric acid. With stirring, the mixture was heated to 94° to 102° C. (at atmospheric pressure) and held at this temperature for 10 minutes. The slurry became clear and was amber colored. Over the course of 30 minutes, the contents of the flask were stripped of water and unreacted diol by vacuum distillation at a temperature of approximately 110° C. and a pressure of 3 mm Hg. The dark brown product solidified when cooled to room temperature. $^{13}$C-NMR spectral analysis showed two peaks at 92.2 and 96.8 indicating the presence of about 25 percent unreacted glucose.

EXAMPLE 3

This example illustrates the preparation of glycidyl glucoglycoside from 3-chloro-2-hydroxypropyl glucoglycoside.

A total of 32 grams of the glycoside of Example 1 was dissolved in 30 ml. of water in a 250 ml. round bottom flask equipped with a magnetic stirrer. The flask and contents were cooled in an ice water bath. While cooling a solution of 3.70 g. of potassium hydroxide in 20 ml. of water was slowly added over a period of about 1 hour to the glycoside solution. The mixture was allowed to warm to room temperature and a pH of 12 was recorded. The mixture was neutralized with 1M hydrochloric acid and stored overnight in a refrigerator. The slightly basic mixture was reneutralized then dissolved in 250 ml of methanol in order to solubilize the glycoside while precipitate the potassium chloride salts produced. After filtration, methanol and water were removed by vacuum distillation leaving the glycidyl glycoside. The presence of the epoxide functionality was confirmed by aqueous magnesium chloride hydrochlorination described in "Organic Analysis", Vol. 1, ed. by J. Mitchell Jr. et al. (Interscience Publishers Inc., New York, 1953) pages 132-134.

EXAMPLE 4

This example illustrates preparation of the 3-chloro-2-hydroxypropyl glycoside of xylose.

Following the reaction and recovery procedure described in Example 1, 40 g. (0.27 mole) of D-xylose, a pentose, was reacted with 118.9 g (1.08 moles) of 3-chloro-1,2-propandiol in the presence of 10 g Dowex 50W-X8 resin (H+ form) for a total of 6 hours.

$^{13}$C-NMR spectral analysis indicated a glycosidic carbon at 99.5 and 104.2 ppm corresponding to an acetal linkage. No signals at 91.9 or 96.3 corresponding to the reducing carbon of pure xylose were present indicating no free xylose remained in the product. Integration of the chloromethyl carbon signal (at 46.8 ppm) and the glycosidic carbon signals indicated that about 50 percent of the product existed as an oligosaccharide glycoside.

EXAMPLE 5

This example illustrates the preparation of the 3-chloro-2-hydroxypropyl glycoside of a maltodextrin containing ten glucose units, referred to as having a D.E. of 10.

The procedure of Example 1 was followed except that the reaction time was reduced to 6 hours and the vacuum distillation step was omitted. The maltodextrin glycoside was recovered in an 84% yield (based on theoretical). The $^{13}$C-NMR spectra of the glycoside product revealed no signals at 92.1 and 95.9 ppm corresponding to the hemi-acetal form of the reducing carbon atom of the maltodextrin. Signals were recorded at 98.6, 99.9, and 102.8 ppm corresponding to the α- and β-glycoside carbon linkages of the maltodextrin. Analysis showed the organic chloride content of the compound to be 2.62% as compared to an expected 2.05% based on the molecular weight of the D.E. 10 glycoside.

EXAMPLE 6

This example illustrates the preparation of the 3-chloro-2-hydroxypropyl glycoside of a maltodextrin containing twenty glucose units, referred to in the art as having a D.E. of 5.

The procedure of Example 1 was followed employing a maltodextrin within a D.E. of 5 (from Anheuser Busch) except the vacuum distillation step was omitted. Due to the reduced solubility of the higher molecular weight maltodextrin of 60° C. in the 3-chloro-1,2-propanediol, the temperature was raised to 80° C. Once dispersed, the mixture was cooled to 60° C. and reacted for five hours. Total reaction time was six hours.

$^{13}$C-NMR analysis showed no reducing carbon atoms present. The chloromethyl carbon signal and α-glycosidic (1,4) carbon of the maltodextrin polymer chain (at 46.6 and 100.7 ppm, respectively) were integrated to show a 1:15 ratio instead of the expected ratio of 1:20. This indicates the presence of some lower molecular weight chlorohydrin glycoside present caused by slight degradation. Organic chlorine analysis of the sample (1.77 vs. 1.02% expected based on molecular weight) confirms this data.

A similar glycoside was prepared with a highly branched maltodextrin (D.E. 5) as compared with the Anheuser Busch dextrin mentioned above.

EXAMPLES 7 & 8

The procedure employed for the preparation of the 3-chloro-2-hydroxypropyl glycoside products of Examples 7 and 8 employing maltose and fructose respectively was essentially identical with that employed in Example 1 with the exception that the reaction time was shortened to 6 hours.

The fructoglycoside depicted below is an example of a glycosidic reagent having a ketal linkage seen here at the reducing $C_2$ carbon atom of the fructose molecule.

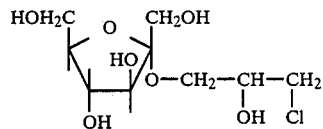

EXAMPLE 9

This example illustrates the preparation of a polysaccharide glycoside when the reaction is carried out employing different catalysts (a cation exchange resin and concentrated (96%) sulfuric acid) and different alcohols (the diol 3-chloro-1,2-propandiol and the simple alcohols methanol and ethanol). The reaction efficiencies of each reaction were compared as well as the degradative effect each reaction had on the polysaccharide. The polysaccharide employed in all reactions was a maltodextrin having a D.E. of 10. Theoretically, the percentage of saccharide converted to glycoside should be 100% and the number of saccharide units of the resultant glycoside product should remain at 10.

Part A. A total of 40 grams of maltodextrin-10 was reacted with 118.5 grams of 3-chloro-1,2-propandiol according to the procedure of Example 5 in the presence of 0.5–4.9 grams (4.9–48.3 meq) of concentrated sulfuric acid. The halohydrin glycosides were compared with the maltodextrin-10 glycoside of Example 5 where a similar amount of the maltodextrin was reacted in the presence of 48.3 meq of Dowex 50W-X8 cation exchange resin. The percentage of saccharide converted to glycoside and the number of saccharide units of the reaction products were calculated based on the organic chloride content of each sample and the ratio of unreacted reducing glycosidic carbon signal intensity to total glycosidic carbon signal intensity of each sample as determined by $^{13}$C-NMR analysis. The results may be found in Table I.

TABLE I

| Reaction | Reactants Alcohol | Catalyst | % Org. Cl | Glycoside Product % Saccharide Converted to Glycoside | # of Saccharide Units (n) |
|---|---|---|---|---|---|
| Theoretical | 3-chloro-1,2-propandiol | — | 2.05 | 100 | 10 |
| 1* | 3-chloro-1,2-propandiol | 48.3 meq Dowex | 2.62 | 100 | 7.6 |
| 2 | 3-chloro-1,2-propandiol | 48.3 meq H$_2$SO$_4$ | 10.07 | 69 | 1 |
| 3 | 3-chloro-1,2-propandiol | 4.9 meq H$_2$SO$_4$ | 4.82 | 87 | 4.5 |

*Sample corresponds to product of Example 5.

The results show that the use of the cation exchange resin as catalyst resulted in a complete reaction (100% conversion to glycoside) with only slight saccharide degradation (n=7.6) while the use of an equivalent amount of sulfuric acid resulted in an incomplete reaction (69% conversion) with severe degradation (n=1). The results of Reaction 3 show that even when a smaller amount of sulfuric acid was employed, the reaction was still incomplete (87% glycoside conversion) and the saccharide was still significantly more degraded (n=4.5) than the saccharide of Reaction 1 which was reacted in the presence of the cation exchange resin.

Part B. A total of 40 grams of maltodextrin-10 was reacted with 71.2 grams methanol or 49.6 grams ethanol in the presence of 48.3 meq of Dowex 50W-X8 or 48.3 meq of concentrated sulfuric acid for 6 hours according to the procedure of Example 5. The methyl and ethyl glycosides were evaluated by $^{13}$C-NMR. The percentage of saccharide converted to glycoside and the number of saccharide units of the reaction products were calculated based on (a) the ratio of —$CH_3$ to —$CH_2OH$ signal intensity of the $C_6$ carbon atoms and (b) the ratio of unreacted reducing glycosidic carbon signal intensity to total glycosidic carbon signal intensity of each sample. The results may be found in Table II.

TABLE II

| Reaction* | Reactants | | Glycoside Product | |
|---|---|---|---|---|
| | Alcohol | Catalyst | % Saccharide Converted to Glycoside | # of Saccharide Units (n) |
| Theoretical | — | — | 100 | 10 |
| 4 | methanol | Dowex | 31 | 5.8 |
| 5 | methanol | $H_2SO_4$ | 85 | 3.0 |
| 6 | ethanol | Dowex | 27 | 7.9 |
| 7 | ethanol | $H_2SO_4$ | 50 | 1.4 |

*The maltodextrin-10 was not soluble in methanol or ethanol after 3 hours at 60° C. The temperature for the remainder of the reactions were adjusted as follows:
Rxns. 4 & 6 - Raised to 80° C. and held for 3 hours, the maltodextrin remaining undissolved in Rxn 4.
Rxn. 5 - Raised to 70° C. for 1 hour then decreased to 60° for remaining 2 hours.
Rxn. 7 - Raised to 70° C. and held for 3 hours.

The results show that when methanol is employed as the alcohol, use of the cation exchange resin results in an incomplete reaction (only 31% conversion) with significant degradation (n=5.8). Use of sulfuric acid resulted in a more complete reaction (85%) with severe degradation. When ethanol was employed in which the maltodextrin is more soluble, the glycoside reaction employing the cation exchange resin did not improve.

Based on the results of Part A and B above it is evident that for the satisfactory preparation of a polysaccharide glycoside, it is necessary to use a cation exchange resin rather than a low molecular weight acid as the catalyst and to use a diol, specifically a 3-halo-1,2-propandiol rather than a simple alcohol. Without employing the combination of the diol and cation exchange resin of the present inventions incomplete reactions and/or significant degradation of the polysaccharide result.

EXAMPLE 10

This example illustrates the preparation of a synthetic homopolysaccharide by reacting corn starch with the 3-chloro-2-hydroxypropyl glucoglycoside from Example 1.

A total of 100 parts of corn starch and 7 parts 3-chloro-2-hydroxypropyl glucoglycoside (dry basis) were added to a solution of 1.6 parts sodium hydroxide and 20 parts sodium sulfate in 150 parts water. The mixture was agitated for 16 hours at 40° C. The pH was then lowered from 12.0 to 5.5 by the addition of 9.3% aqueous hydrochloric acid. The starch derivative was recovered by filtration, washed three times with acidic water (pH 5.5) and air dried.

Aqueous slurries containing 7.7 percent (based on dry basis) of the derivatized starch product or its underivatized base were cooked for comparison in a boiling water bath for 20 minutes. The gelatinized cooks stood overnight at room temperature before examination. The corn base cook produced a firm gel. The derivatized starch cook, on the other hand, did not form a gel but was stabilized. See Table III for gelatinization temperature data.

EXAMPLE 11

This example illustrates the preparation of a synthetic homopolysaccharide by reacting waxy maize starch with the glucoglycoside from Example 1.

One hundred parts waxy maize starch and 8.5 parts glucoglycoside (dry basis) were reacted as described in Example 10. A comparison of 6.25 percent (based on dry basis) aqueous slurries of the derivatized waxy maize product and its underivatized base after cooking was made as in Example 10. The two cooks were identical indicating no inhibition (crosslinking) of the derivatized waxy maize product. See Table III for gelatinization temperature data.

EXAMPLE 12

Using the procedure of Example 10, a number of starch derivatives were prepared with variations in treatment level of the glucoglycoside reagent of Example 1 and starch based used. The data, including gelatinization temperatures is summarized in Table III. It is noted that in all cases as the glycoside treatment level increases, the starch gelatinization temperature decreases indicating the stabilizing effect the derivatization has on the starch.

TABLE III

| Starch Base | % Glucoglycoside* | Gelatinization Temp. (°C.) |
|---|---|---|
| Corn | 0 | 71 |
| Corn | 7.0 | 66 |
| Corn | 14.0 | 64.5 |
| Waxy Maize | 0 | 69 |
| Waxy Maize | 8.5 | 66 |
| Waxy Maize | 17.0 | 64 |
| Tapioca | 0 | 65 |
| Tapioca | 6.5 | 62 |
| Tapioca | 13.0 | 59.5 |
| Potato | 0 | 62 |
| Potato | 6.5 | 59 |
| Potato | 13.0 | 55 |

*based on dry basis weight.

EXAMPLE 13

Corn starch was reacted with 30 parts (as is) of the maltodextrin-10 glycoside of Example 5 employing the reaction procedure of Example 10. The starch derivative had a gelatinization temperature of 65° C. as compared to 69° C. for the underivatized base starch.

EXAMPLE 14

This example illustrates the preparation of a synthetic homopolysaccharide prepared by reacting a cationic corn starch derivative with the glucoglycoside of Example 1.

The cationic starch ether derivative was prepared by adding a total of 6.3 parts of a 50% aqueous solution of 2-diethylaminoethylchloride hydrochloride and 2.0 parts calcium hydroxide to a slurry of 100 parts corn starch and 125 parts water. The mixture was agitated at 40° C. for 6 hours and the pH was lowered to 3.0 with 9.3% aqueous hydrochloric acid. It was recovered by filtration, washed with water three times, air dried and then treated with 7.5% glucoglycoside as in Example 10.

The gelatinization temperature of the cationic starch was 64.5° C. After treatment with the glycoside reagent, the starch product had a gelatinization temperature of 63° C.

EXAMPLE 15

This example illustrates the preparation of a synthetic homopolysaccharide prepared by reacting a crosslinked waxy maize starch with the glucoglycoside of Example 1.

The crosslinked starch was prepared by adding 100 parts waxy maize to a solution of 0.8 parts sodium hydroxide, and 150 parts water in a sealable vessel. The vessel was sealed quickly after 0.025 parts epichlorohydrin was added to the starch slurry. The mixture was agitated at 40° C. for 16 hours, cooled, then the pH was lowered to 5 with 9.3% aqueous hydrochloric acid. It was recovered by filtration, washed with water, dried, and treated with 7.5% glucoglycoside as in Example 10.

The gelatinization temperature of the crosslinked starch was 69° C. After treatment with the glycoside reagent, the starch product had a gelatinization temperature of 66.5° C.

EXAMPLE 16

This example illustrates the preparation of a synthetic heteropolysaccharide prepared by reacting guar gum with the 3-chloro-2-hydroxypropyl glucoglycoside from Example 1.

A total of 60 grams of isopropanol and 18.2 grams of a 17.5% aqueous solution of sodium hydroxide were added to a 250 ml round bottom flask equipped with a mechanical stirrer and condensor. While stirring, 50 grams of unpurified guar gum and then 10 grams of the glycoside (8.0 g dry basis) were added. The reaction mixture was stirred for 6 hours at 60° C., cooled to room temperature, then neutralized (pH=6.5) with citric acid. The novel guar gum derivative was recovered by filtration, washed three times with 70% aqueous ethanol and once with ethanol then air dried.

In order to qualitatively analyze for the presence of the glucose glycoside derivatization on the guar, a portion of the derivative was hydrolyzed with hydrochloric acid in order to cleave a majority of the guar into its monosaccharide units of mannose and galactose. The hydrolyzed samples was further derivatized with n-trimethylsilyl-imidazole and analyzed by gas chromatography/mass spectrometry employing an SP 2100 column. The sample was evaluated at 185° C. at a flow rate of 40 ml/min. The signals for both $\alpha$- and $\beta$-glucose from the glycoside derivitization were identified along with the galactose and mannose signals from the guar.

EXAMPLE 17

This example illustrates the preparation of a synthetic heretopolysaccharide prepared by reaction guar gum with the maltodextrin-10 glycoside of Example 5.

A total of 30 grams of unpurified guar gum was added to an apparatus as described in Example 16 which contained 50 grams of isopropanol and 11.6 grams of a 16% aqueous solution of sodium hydroxide. The maltodextrin-glycoside (10 grams, as is) was then added. The reaction mixture was held at 60° C. for 16 hours. The mixture was cooled then adjusted to a pH of 6.5 with citric acid, filtered, and washed with ethanol.

A 1% solids aqueous dispersion of the guar derivative was dialyzed. The derivative, still in dispersion, was then treated with $\beta$-amylase (an enzyme specific for cleaving polyglucose chains into disaccharide maltose units) in order to cleave the maltodextrin side chains on the guar molecule while leaving the galactomannan structure intact. The dispersion was again dialyzed. The dialyzate was concentrated then treated with n-trimethylsilyl-imidazole and analyzed by gas chromatography as described above. Signals for maltose as well as for small amounts of $\alpha$- and $\beta$-glucose, all attributable to the glycoside derivatization, were identified.

We claim:

1. An improved process for preparing a 3-halo-2-hydroxypropyl glycoside by reacting a polysaccharide having from 2 to about 20 saccharide units, said polysaccharide containing a reducing carbon atoms, with an excess of 3-halo-1,2-propandiol in the presence of a catalyst, wherein the improvement comprises carrying out the reaction in the presence of a cation exchange resin as the sole catalyst, said cation exchange resin providing improved conversion efficiency and minimal degradation.

2. The process of claim 1, wherein the 3-halo-1,2-propandiol is 3-chloro-1,2-propandiol or 3-bromo-1,2-propandiol and the polysaccharide is selected from the group consisting of maltose, and a maltodextrin having a dextrose equivalent of 5 to 10.

3. The process of claim 1, wherein the cation exchange resin is a sulfonated cross-linked polystyrene.

4. The process of claim 1, wherein the reaction is carried out at a temperature of 55°-80° C. for about 3 to 20 hours.

5. The process of claim 1, wherein one part of the resin is employed for every 2 to 8 parts of the polysaccharide.

6. The process of claim 1, further comprising reacting the 3-halo-2-hydroxypropyl glycoside with an alkali metal hydroxide in order to form a corresponding glycidyl glycoside.

7. A process for preparing a 3-halo-2-hydroxypropyl glycoside comprising reacting a polysaccharide with an excess of 3-halo-1,2-propandiol in the presence of a cation exchange resin as the sole catalyst, said polysaccharide having a reducing carbon atom and consisting of 2 to about 20 saccharide units, said reaction carried out at a temperature of 60°-65° C.

8. The process of claim 7, wherein the 3-halo-1,2-propandiol is 3-chloro-1,2-propandiol or 3-bromo-1,2-propandiol.

9. The process of claim 7, wherein the cation exchange resin is a sulfonated cross-linked polystyrene.

10. The process of claim 7, wherein the polysaccharide is a maltodextrin having a dextrose equivalent of 5 to 10.

11. A starch ether having a pendant saccharide side chain, which has the structure St—O—CH$_2$—CH(OH)—CH$_2$—O— (saccharide)$_n$, wherein St—O represents a starch molecule with the oxygen being linked to the starch molecule by an ether linkage and wherein (saccharide)$_n$ represents a saccharide unit with n being 1-20 and with the oxygen being linked to the reducing glycosidic carbon atom of (saccharide)$_n$ by an acetal or ketal linkage.

12. The starch ether of claim 11 wherein the saccharide unit of (saccharide)$_n$ is selected from the group consisting of glucose, xylose, and fructose.

13. The starch ether of claim 12 wherein the saccharide unit of (saccharide)$_n$ is glucose and n is 1 to 10.

14. A gum ether having a pendant saccharide side chain, which has the structure Gum—O—CH$_2$—CH- (OH)—CH₂—O— (saccharide)$_n$, wherein Gum—O represents a gum molecule with the oxygen being linked to the gum molecule by an ether linkage and wherein (saccharide)$_n$ represents a saccharide unit with n being 1-20 and with the oxygen being linked to the reducing glycosidic carbon atom of (saccharide)$_n$ by an acetal or ketal linkage.

15. The gum ether of claim 14, wherein the gum is a polygalactomannan gum selected from the group consisting of guar gum and locust bean gum.

16. The gum ether of claim 15, wherein the gum is guar gum, the saccharide unit of (saccharide)$_n$ is glucose, and n is 1 to 10.

17. A polysaccharide ether having a pendant saccharide side chain, which has the structure P—O—CH₂—CH(OH)—CH₂—O— (saccharide)$_n$, wherein P—O represents a polysaccharide molecule selected from the group consisting of starch and plant gums with the oxygen being linked to the polysaccharide molecule by an ether linkage and (saccharide)$_n$ represents a saccharide unit with n being 1-20 and with the oxygen being linked to the reducing glycosidic carbon atom of (saccharide)$_n$ by an acetal or ketal linkage.

18. The polysaccharide ether of claim 17, wherein the polysaccharide molecule P—O is starch.

* * * * *